United States Patent

Vanden Eynde et al.

[11] 3,947,272
[45] Mar. 30, 1976

[54] SILVER HALIDE EMULSIONS CONTAINING 2-PYRAZOLON-5-ONE PHOTOGRAPHIC COLOUR COUPLERS

[75] Inventors: Hector Alfons Vanden Eynde, Edegem; Raphael Karel Van Poucke, Berchem, both of Belgium

[73] Assignee: AGFA-GEVAERT, N.V., Mortsel, Belgium

[22] Filed: Mar. 18, 1974

[21] Appl. No.: 452,326

[30] Foreign Application Priority Data
Apr. 6, 1973  United Kingdom............... 16627/73

[52] U.S. Cl. .................... 96/56.5; 96/56.6; 96/100
[51] Int. Cl.² ...................... G03C 7/00; G03C 1/40
[58] Field of Search..................... 96/56.5, 100, 56.6

[56] References Cited
UNITED STATES PATENTS

| | | |
|---|---|---|
| 2,343,703 | 3/1944 | Porter et al............................ 96/100 |
| 3,462,270 | 8/1969 | Eynde et al........................... 96/100 |
| 3,563,745 | 2/1971 | Eynde et al........................... 96/100 |
| 3,567,449 | 3/1971 | Eynde et al........................... 96/100 |

*Primary Examiner*—J. Travis Brown
*Attorney, Agent, or Firm*—A. W. Breiner

[57] ABSTRACT

Novel magenta forming colour couplers for use in silver halide colour photography are described which correspond to the formula:

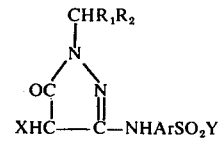

wherein
$R_1$ represents hydrogen, alkyl or aryl; $R_2$ represents fluoroalkyl, cyanoalkyl or phenyl; X is hydrogen or a displaceable group; Ar represents phenylene and Y represents alkyl, aryl, alkylamino, arylamino or alkylarylamino.

13 Claims, No Drawings

SILVER HALIDE EMULSIONS CONTAINING 2-PYRAZOLON-5-ONE PHOTOGRAPHIC COLOUR COUPLERS

The present invention relates to 2-pyrazolon-5-one colour couplers, to the preparation thereof, to photographic silver halide elements and developing compositions containing such colour couplers as well as to colour development processes wherein said colour couplers take part in the formation of a magenta dye image.

It is known that for the formation of a photographic colour image in a light-sensitive silver halide emulsion layer the exposed silver halide is developed by means of an aromatic primary amino colour developer in the presence of a colour coupler which by reaction with the oxidized developer forms a dye on the areas corresponding to the silver image.

In subtractive three-colour photography it is common practice to use a photographic element comprising at least one red-sensitized, green-sensitized and blue-sensitive silver halide emulsion layer, wherein upon development in the presence of suitable colour couplers, cyan, magenta and yellow dye images are formed respectively.

It is desirable that colour couplers employed in colour photography have good coupling activity, and produce dye images that have the desired spectral absorption characteristics and favourable stability against light, heat and moisture.

Colour couplers may be of the diffusible type or of the non-diffusible type. By diffusible couplers is meant colour couplers the dispersability or solubility of which is sufficient to enable them to be usefully incorporated in aqueous colour developing solutions whereas by non-diffusible colour couplers is meant colour couplers intended for use in the photographic element where they should remain during colour development. Non-diffusible colour couplers are usually obtained by providing in the colour coupler molecule one or more ballasting groups which are sufficiently large to prevent diffusion of the colour coupler e.g. aliphatic groups of 5 to 20 C-atoms.

It is known that for homogeneously distributing non-diffusible colour couplers in a hydrophilic colloid layer, more particularly a silver halide emulsion layer, special techniques are to be used. Colour couplers containing a water-solubilizing group e.g. a sulpho group can be incorporated in the hydrophilic colloid compositions from alkaline solutions if necessary in the presence of a water-miscible solvent e.g. ethanol. Water-insoluble or sparingly water-soluble colour couplers can be incorporated in hydrophillic colloid compositions by dispersing techniques using high-boiling water-immiscible solvents e.g. tricresyl phosphate and dibutylphthalate and/or low boiling water-immiscible solvents e.g. methylene chloride, ethyl acetate, diethyl carbonate, etc. No matter what technique is used, the colour couplers should be homogeneously distributed in the hydrophilic colloid layer and have high stability against crystallization so that colour image formation is not impaired.

For the formation of the magenta separation image it is known to use 2-pyrazolin-5-one colour couplers. In U.S. Pat. Nos. 3,462,270, 3,563,745 and 3,567,449 2-pyrazolin-5-one colour couplers carrying in the 1-position a fluoroalkyl, a β-cyanoalkyl or a benzyl group respectively have been described. Though these 1-substituted 2-pyrazolin-5-one colour couplers are generally satisfactory it is desirable to improve the spectral absorption characteristics of the dyes formed upon colour development. It is also desirable to improve the ability of the non-diffusible types for being incorporated in hydrophilic colloid media by means of dispersion techniques.

In accordance with the present invention novel 2-pyrazolin-5-one colour couplers carrying in the 1-position a fluoroalkyl, β-cyanoalkyl or benzyl group are provided which yield upon colour development azomethine dyes having favourable sensitometric and spectral properties with high transmission for blue and red light and favourable stability against light, heat and moisture. Moreover, the non-diffusible types of the colour couplers of the present invention lend themselves very well for being incorporated in hydrophilic colloid compositions, more particularly a silver halide emulsion, by means of dispersion techniques and stable, finely divided dispersions of the colour couplers in the emulsion layers can be obtained in this way.

The novel colour couplers of the present invention can be represented by the formula:

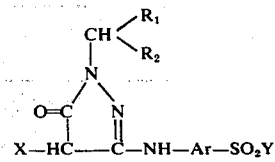

wherein:

$R_1$ represents hydrogen, alkyl e.g. lower alkyl such as methyl or aryl e.g. phenyl, $R_2$ represents a fluoroalkyl group $X(CF_2)_n-$ with $X = $ H or F and $n = 1$ to 10, an α-cyanoalkyl group e.g. cyanomethyl, α-cyanoethyl and α,γ-dicyanopropyl or a phenyl group preferably a phenyl group with one or more electron-withdrawing substituents e.g. a halogen atom e.g. chlorine, a cyano group, a trifluoromethyl group, an alkylsulphonyl group e.g. methylsulphonyl, a sulphamoyl group, etc., X represents hydrogen or a substituent that exhibits two-equivalent character on colour development e.g. a halogen atom e.g. chlorine atom, an alkylthio, arylthio, or heterocyclic thio group, an alkoxy, aryloxy or acyloxy group, a sulpho group or an arylazo group, Ar represents phenylene including substituted phenylene e.g. phenylene substituted with halogen e.g. chlorine or alkoxy e.g. methoxy, and Y represents alkyl, aryl, monoalkylamino, monoarylamino, dialkylamino or alkylarylamino.

The term "two-equivalent character" as applied to colour coupling systems is well known and is described for example in "The theory of the photographic process" C.E.K. Mees, the Mac-Millan Company, N.Y., 1966, p. 390. It means that by the presence of the splittable substituent on the active methylene group only two equivalents of silver are needed for the formation of the dye contrary to four equivalents when the methylene group is not substituted.

The colour couplers of the present invention may be of the diffusible or non-diffusible type as described above.

The invention is particularly concerned with non-diffusible colour couplers for use in the photographic colour element itself. For this purpose it is preferred that the group Y in the above general formula is or comprises a ballasting aliphatic straight-chain or branched-chain hydrocarbon group of at least 5 C-atoms. The non-diffusible colour couplers of the invention lend themselves very well for being incorporated in the silver halide emulsion by dispersion techniques.

The present invention provides besides novel 2-pyrazolin-5-one compounds, a method of producing a magenta coloured photographic image in a photographic light-sensitive silver halide material which comprises exposing the material and developing it with an aromatic primary amino colour developing agent in the presence of a 2-pyrazolin-5-one colour coupler as defined above.

The present invention further provides a photographic element containing at least one silver halide emulsion layer and a 2-pyrazolin-5-one colour coupler as defined above wherein the group Y is or comprises an aliphatic hydrocarbon group of at least 5 C-atoms.

The colour couplers of the present invention can be prepared according to methods well known in the art. For example, they can be prepared by reaction of the fluoroalkyl, β-cyanoalkyl and benzyl hydrazines known from the above U.S. Patents with an appropriately substituted aniline and ethyl β, β, β-trimethoxypropionate according to the method described in the published German patent application No. 2,042,920.

The anilines carrying N-substituted sulphamoyl groups can be prepared by means of one of the following procedures :

1. reaction of a nitrobenzene sulphochloride with a primary or secondary amine in methylene chloride using sodium hydroxide as hydrogen chloride acceptor, followed by catalytic hydrogenation of the nitro compound formed, and 2. reaction of an acetylamino benzene sulphochloride with a primary or secondary amine in methylene chloride using sodium hydroxide as hydrogen chloride acceptor, followed by deacetylation.

The anilines carrying alkyl- or arylsulphonyl groups can e.g. be prepared by the following procedure :

3. alkylation or arylation of an appropriate thioacetanilide followed by oxidation and deacetylation.

Representative anilines prepared according to one of the above procedures and useful for the preparation of the colour couplers of the present invention are listed in the following table I.

Table 1

| Amine | Procedure | Melting point °C |
|---|---|---|
| 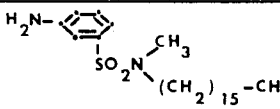 | 1 | 67 |
| 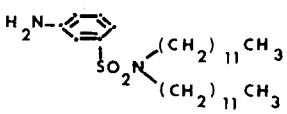 | 1 | oily liquid |
| 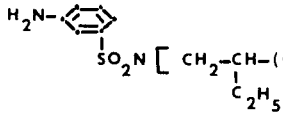 | 1 | 39 |
| 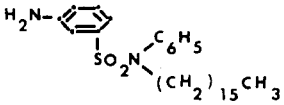 | 1 | 69 |
| 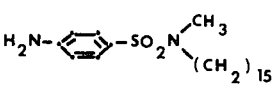 | 1 | 73 |
| 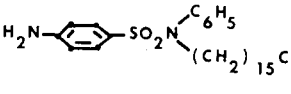 | 1 | 85 |
| 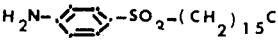 | 3 | 119 |

Table 1-continued

| Amine | Procedure | Melting point °C |
|---|---|---|
| (structure: 4-amino-3-chloro-N-methyl-N-hexadecyl-benzenesulfonamide) | 1 | 62 |
| (structure: 4-amino-3-chloro-N-phenyl-N-hexadecyl-benzenesulfonamide) | 1 | 72 |
| (structure: 4-amino-3-hexadecyloxy-N-phenyl-benzenesulfonamide) | 1 | 70 |
| (structure: 4-amino-3-methoxy-N-hexadecyl-benzenesulfonamide) | 2 | 80 |

The following preparations illustrate how the colour couplers of the present invention can be prepared. Representative examples of colour couplers are listed in table II hereinafter.

PREPARATION 1 : COLOUR COUPLER 2 OF TABLE II 123 g (0.3 mole) of amine 1 of table I in 300 ml of acetic acid and 86.4 g (0.36 mole) of ethyl $\beta,\beta,\beta$-trimethoxy propionate (for 80 % pure) were stirred for 90 min.

The excess of acetic acid and propionate was removed by evaporation under reduced pressure (1 mm Hg) at 100°–110°C.

57 g (0.3 mole) of α-trifluoromethyl benzylhydrazine and 2 ml of acetic acid were added to the residue. The reaction mixture was stirred for 90 min. at 100°–110°C whereupon it was concentrated by evaporation until dry. The residue was recrystallized from 525 ml of methanol.

Yield : 93.5 g (48 %). Melting point : 101°–102°C.

PREPARATION 2 : COLOUR COUPLER 11 OF TABLE II 47.2 g (0.1 mole) of amine 4 of table I and 0.12 mole of ethyl $\beta,\beta,\beta$-trimethoxypropionate were allowed to react in 100 ml of acetic acid as described in preparation 1.

After evaporation, 11.4 g (0.1 mole) of 2,2,2-trifluoroethylhydrazine and 1 ml of acetic acid were added. The reaction mixture was heated for 90 min. at 100–110°C. It became solid and was recrystallized from 150 ml of acetic acid.

Yield : 41.5 g (65 %). Melting point : 138°C.

PREPARATION 3 : COLOUR COUPLER 12 OF TABLE II

This coupler was prepared from 41 g (0.1 mole) of amine 5 of table I, 100 ml of acetic acid, 0.12 mole of ethyl $\beta,\beta,\beta$-trimethoxypropionate and 19.1 g (0.1 mole) of 3,4-dichlorobenzyl hydrazine, according to the procedure of preparation 1. The residue was recrystallized first from ethanol and then from methyl acetate.

Yield : 42.5 g (65.3 %). Melting point : 110°C.

PREPARATION 4 : COLOUR COUPLER 16 OF TABLE II 89.9 g (0.2 mole) of amine 8 of table I and 0.24 mole of ethyl $\beta,\beta,\beta$-trimethoxypropionate were allowed to react in 200 ml of acetic acid as described in preparation 1.

After evaporation, 200 ml of acetic acid and 38 g (0.2 mole) of α-trifluoromethyl benzylhydrazine were added. The temperature was kept at 20°C for 5 hours.

After standing overnight, the precipitate formed was filtered by suction and recrystallized from 275 ml of acetonitrile.

Yield : 80 g (58.6 %). Melting point : 93°C.

Table II

| Colour coupler | Substituent in 1-position | 3-position derived from | Melting point °C | Yield % |
|---|---|---|---|---|
| 1 | —CH$_2$CF$_3$ | amine 5 | 135 | 27.8 |
| 2 | 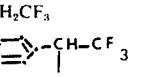 | amine 1 | 102 | 48 |
| 3 | —CH$_2$CF$_3$ | amine 7 | 138 | 52.5 |
| 4 | 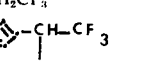 | amine 5 | 101–103 | 37 |
| 5 | idem | amine 3 | 106 | 20 |
| 6 | idem | amine 2 | 90 | 40 |
| 7 | idem | amine 7 | 149 | 27.5 |
| 8 | 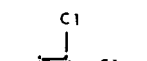 | amine 1 | 117–118 | 37.5 |
| 9 | —CH$_2$CF$_3$ | amine 1 | 106 | 37.5 |
| 10 | 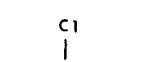 | amine 1 | 98 | 50 |
| 11 | —CH$_2$CF$_3$ | amine 4 | 138 | 65 |
| 12 | 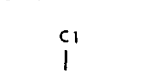 | amine 5 | 110 | 65.5 |
| 13 | —CH$_2$CF$_3$ | amine 6 | 153 | 66 |
| 14 | 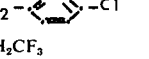 | amine 8 | 109 | 47 |
| 15 | —CH$_2$CF$_3$ | amine 8 | 75 | 56 |
| 16 |  | amine 8 | 93 | 58.6 |
| 17 | —CH$_2$CF$_3$ | amine 9 | 124 | 60.5 |
| 18 |  | amine 9 | 128–129 | 20 |
| 19 | —CH$_2$CF$_3$ | amine 10 | 160 | 50 |
| 20 |  | amine 10 | 142 | 30 |
| 21 | —CH$_2$CF$_3$ | amine 11 | 160 | 50 |
| 22 |  | amine 11 | 174 | 35 |

The non-diffusible colour couplers according to the present invention can be incorporated into the photographic silver halide element according to any suitable technique known in the art. The colour couplers of the invention are preferably incorporated into photographic hydrophilic colloid media from solutions in high boiling sparingly water-miscible solvents such as di-n-butyl phthalate and tricresyl phosphate or in low-boiling sparingly water-miscible solvents such as ethyl acetate, methylene chloride, diethyl carbonate, chloroform, etc. or mixtures thereof in that they have a high solubility therein and very fine dispersions can be obtained by means of these solvents.

For this purpose these solutions can be dispersed in extremely fine droplets, preferably in the presence of one or more wetting or dispersing agents into a hydrophilic colloid medium e.g. aqueous gelatin or into water, the low-boiling sparingly water-miscible solvent then being removed by evaporation. The stable dispersions of the colour couplers can be stored as such and then admixed whenever desired with coating composition itself of the hydrophilic colloid layer such as a silver halide emulsion layer into which the compounds are intended to be present.

Of course the compounds of the invention can also be incorporated into the hydrophilic colloid media in other ways.

More details about particularly suitable techniques that may be employed for incorporating the colour couplers of the invention into a hydrophilic colloid layer of a photographic material there can be referred to e.g. U.S. patent specification Nos. 2,269,158, 2,284,887, 2,304,939, 2,304,940 and 2,322,027; U.K. patent specification Nos. 791,219, 1,098,594, 1,099,414, 1,099,415, 1,099,416, 1,099,417, 1,218,190, 1,272,561 and 1,297,347; French patent specification No. 1,555,663; Belgian patent specification No. 722,026; German patent specification No. 1,127,714 and to U.K. patent specification No. 1,297,947.

The couplers according to the invention may be used in conjunction with various kinds of photographic emulsions. Various silver salts may be used as the sensitive salt such as silver bromide, silver iodide, silver chloride or mixed silver halides such as silver chlorobromide, silver bromoiodide and silver chlorobromoiodide. The couplers can be used in emulsions of the mixed packet type as described in U.S. patent specification No. 2,698,794 or emulsions of the mixed grain type as described in U.S. patent specification No. 2,592,243. The colour couplers can be used with emulsions wherein latent images are formed predominantly on the surface of the silver halide crystal, or with emulsions wherein latent images are formed predominantly inside the silver halide crystal.

The hydrophilic colloid used as the vehicle for the silver halide may be, for example, gelatin, colloidal albumin, zein, casein, a cellulose derivative, a synthetic hydrophilic colloid such as polyvinyl alcohol, poly-N-vinyl pyrrolidone, etc. If desired, compatible mixtures of two or more of these colloids may be employed for dispersing the silver halide.

The light-sensitive silver halide emulsions of use in the preparation of a photographic material according to the present invention may be chemically as well as optically sensitized. They may be chemically sensitized by effecting the ripening in the presence of small amounts of sulphur containing compounds such as allyl thiocyanate, allyl thiourea, sodium thiosulphate, etc. The emulsions may also be sensitized by means of reductors for instance tin compounds as described in French patent specification No. 1,146,955 and in Belgian patent specification No. 568,687, imino-amino methane sulphinic acid compounds as described in U.K. patent specification No. 789,823 and small amounts of noble metal compounds such as gold, platinum, palladium, iridium, ruthenium and rhodium compounds. They may be optically sensitized by means of cyanine and merocyanine dyes.

The said emulsions may also comprise compounds which sensitize the emulsions by development acceleration for example compounds of the polyoxyalkylene type such as alkylene oxide condensation products as described among others in U.S. patent specification Nos. 2,531,832, 2,533,990, 3,210,191 and 3,158,484; in U.K. patent specification Nos. 920,637 and 991,608 and in Belgian patent specification No. 648,710 and onium derivatives of amino-N-oxides as described in U.K. patent specification No. 1,121,696.

Further, the emulsions may comprise stabilizers e.g. heterocyclic nitrogen-containing thioxo compounds such as benzothiazoline-2-thione and 1-phenyl-2-tetrazoline-5-thione and compounds of the hydroxytriazolopyrimidine type. They can also be stabilized with mercury compounds such as the mercury compounds described in Belgian patent specification Nos. 524,121, 677,337 and 707,386 and in U.S. patent specification No. 3,179,520.

The light-sensitive emulsions may also comprise all other kinds of ingredients such as plasticizers, hardening agents, wetting agents, etc.

The non-diffusing magenta colour formers described in the present invention are usually incorporated into the green-sensitized silver halide emulsion for forming one of the differently sensitized silver halide emulsion layers of a photographic multilayer colour material. Such photographic multilayer colour material usually comprises a support, a red-sensitized silver halide emulsion layer with a cyan colour former, a green-sensitized silver halide emulsion layer with a magenta colour former and a blue-sensitive silver halide emulsion layer with a yellow colour former.

The emulsions can be coated on a wide variety of photographic emulsion supports. Typical supports include cellulose ester film, polyvinylacetal film, polystyrene film, polyethylene terephthalate film and related films or resinous materials, as well as paper and glass. It is also possible to employ paper coated with α-olefin polymers e.g. paper coated with polyethylene, polypropylene, ethylene-butylene copolymers, etc.

For the production of photographic colour images according to the present invention an exposed silver halide emulsion layer is developed with an aromatic primary amino developing substance in the presence of a colour coupler according to the present invention. All colour developing agents capable of forming azomethine dyes can be utilised as developers. Suitable developing agents are aromatic compounds such as p-phenylene diamine and derivatives for example N,N-diethyl-p-phenylene diamine, N-butyl-N-sulphobutyl-p-phenylene diamine, N,N-diethyl-N'-sulphomethyl-p-phenylene diamine, N,N-diethyl-N'-carboxymethyl-p-phenylene diamine, 2-amino-5-diethylaminotoluene, 4-amino-N-ethyl-N(β-methanesulphonamido-ethyl)-m-toluidine, N-hydroxyethyl-N-ethyl-p-phenyle diamine, etc.

The following examples illustrate the present invention.

EXAMPLE 1

A dispersion in aqueous gelatin of colour coupler 2 having the following structural formula :

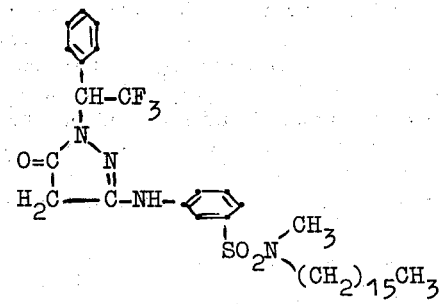

was prepared by dispersing a solution of 12 g of colour coupler in 30 ml of ethyl acetate, in 100 ml of 10 % aqueous gelatin comprising 1 g of the sodium salt of laurylbenzene sulphonate and then removing the ethyl acetate by evaporation under reduced pressure.

The dispersion was admixed with a green-sensitized silver bromide emulsion comprising per kg 19.25 g of silver bromide and 77 g of gelatin.

The emulsion was coated on a transparent film support and exposed, after drying, through a grey wedge for 1/20 sec. The exposed material was developed for 8 min. at 20°C in the following composition :

| | |
|---|---|
| N-butyl-N-ω-sulphobutyl-p-phenylenediamine | 6 g |
| hydroxylamine hydrochloride | 4 g |
| anhydrous sodium sulphite | 4 g |
| potassium carbonate | 100 g |
| potassium bromide | 1 g |
| water to make | 1 liter. |

The material was then bleached and fixed in the usual way to leave a magenta wedge image having absorption maximum at 530 nm.

EXAMPLE 2

Example 1 was repeated with the only difference that development now took place in the following composition :

| 2-amino-5-[N-ethyl-N(β-methylsul- | |
|---|---|
| phenylamino)ethyl] | 2 g |
| anhydrous sodium sulphite | 0.5 g |
| anhydrous sodium carbonate | 30 g |
| water to make | 1 liter |

A magenta wedge image was obtained having absorption maximum at 534 nm.

EXAMPLE 3

To 50 ml of a green-sensitized silver halide emulsion as described in example 1, 5 g of colour coupler 3 having the following structural formula :

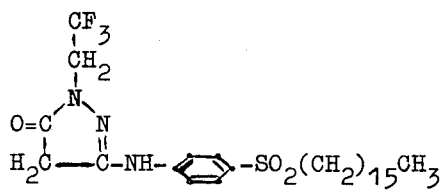

was added from a gelatin dispersion prepared by dispersing a solution of the colour coupler in 15 ml of ethyl acetate and 15 g of tri-o-cresyl phosphate in 50 ml of 10 % aqueous gelatin comprising 0,5 g of the sodium salt of laurylbenzene sulphonate and then removing the ethyl acetate by evaporation under reduced pressure.

After coating the emulsion on a support and drying the layer, the emulsion was exposed and developed as described in examples 1 and 2 to yield magenta wedge images having absorption maxima at 528 nm and 536 nm respectively.

After development in the following composition :

| 2-amino-5-diethylaminotoluene | |
|---|---|
| hydrochloride | 2.5 g |
| anhydrous sodium sulphite | 5 g |
| anhydrous sodium carbonate | 20 g |
| potassium bromide | 2 g |
| water to make | 1 liter | a magenta wedge image having absorption maximum at 534 nm was obtained.

EXAMPLE 4

17 g of colour coupler 1 having the following structural formula :

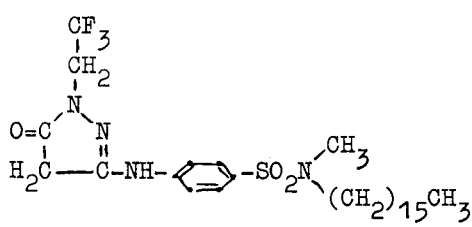

were dissolved in 50 g of tri-o-cresylphosphate and 50 ml of ethyl acetate. The solution was dispersed in 170 ml of 10 % aqueous gelatin comprising 1.7 g of the sodium salt of laurylbenzene sulphonate, whereupon the ethyl acetate was removed by evaporation under reduced pressure.

The gelatin dispersion of colour coupler 1 was admixed with a green-sensitized silver halide emulsion comprising per kg 30 g of silver bromide and 105 g of gelatin.

After coating, exposure and development as described in examples 1 and 2 magenta wedge images were obtained having absorption maxima at 530 nm and 536 nm respectively.

EXAMPLE 5

13 g of colour coupler 4 having the following structural formula :

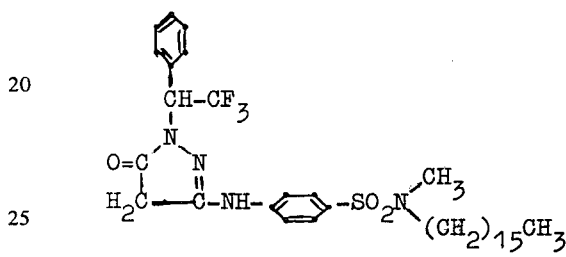

were dissolved in 36 g of tri-o-cresyl phosphate and 36 ml of ethyl acetate. The solution was dispersed in 130 ml of 10 % aqueous gelatin comprising 1.3 g of the sodium salt of laurylbenzene sulphonate. The ethyl acetate was then removed by evaporation under reduced pressure.

The gelatin dispersion of colour coupler 4 was then admixed with 500 g of a green-sensitized silver bromoiodide (3 mole % of iodide) emulsion comprising 0.115 mole of silver halide.

The emulsion was coated and exposed as described in example 1.

After development in the compositions of examples 1, 2 and 3 respectively magenta wedge images were obtained having absorption maxima at 532 nm, 538 nm and 528 nm respectively.

We claim:

1. Method of producing a magenta coloured photographic image in a photographic light-sensitive silver halide material which comprises exposing the material and developing it with an aromatic primary amino colour developing agent in the presence of a 2-pyrazolin-5-one colour coupler corresponding to the formula :

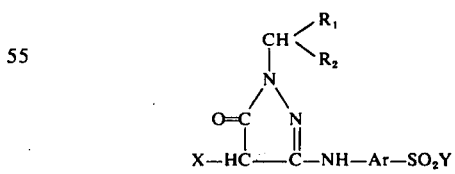

wherein :

$R_1$ represents hydrogen, alkyl or aryl, $R_2$ represents a fluoroalkyl group $X(CF_2)_n-$ wherein X is hydrogen or fluorine and $n$ is 1 to 10, an α-cyanoalkyl group, or a phenyl group, X represents hydrogen or a substituent that exhibits 2-equivalent character, Ar represents a phenylene group, and Y represents an alkyl group, an aryl group, a monoalkylamino group, a monoarylamino group, a dialkylamino group or an alkylarylamino group.

2. Method according to claim 1, wherein the colour coupler is present in the light-sensitive material and is one wherein Y is or comprises an aliphatic hydrocarbon group of at least 5 C-atoms.

3. A photographic element containing at least one silver halide emulsion layer and a 2-pyrazolin-5-one colour coupler corresponding to the formula:

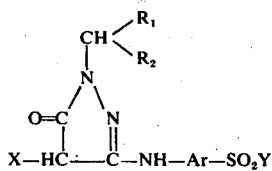

wherein:
$R_1$ represents hydrogen, alkyl or aryl,
$R_2$ represents a fluoroalkyl group $X(CF_2)_n-$ wherein X is hydrogen or fluorine and $n$ is 1 to 10, an α-cyanoalkyl group, or a phenyl group,
X represents hydrogen or a substituent that exhibits 2-equivalent character,
Ar represents a phenylene group, and
Y represents an alkyl group, an aryl group, a monoalkylamino group, a monoarylamino group, a dialkylamino group or an alkylarylamino group.

4. The method according to claim 1 wherein Y is a monoalkylamino group.

5. The method according to claim 1 wherein Y is a monoarylamino group.

6. The method according to claim 1 wherein Y is a dialkylamino group.

7. The method according to claim 1 wherein Y is an alkylarylamino group.

8. The method according to claim 1 wherein X is a member of the group consisting of hydrogen, a halogen atom, alkylthio, arylthio, heterocyclic thio, alkoxy, aryloxy, acyloxy, sulpho, and arylazo.

9. The photographic element according to claim 3 wherein Y is a monoalkylamino group.

10. The photographic element according to claim 3 wherein Y is a monoarylamino group.

11. The photographic element according to claim 3 wherein Y is a dialkylamino group.

12. The photographic element according to claim 3 wherein Y is an alkylarylamino group.

13. The photographic element according to claim 3 wherein X is a member of the group consisting of hydrogen, a halogen atom, alkylthio, arylthio, heterocyclic thio, alkoxy, aryloxy, acyloxy, sulpho, and arylazo.

* * * * *